United States Patent
Nguyen

[11] Patent Number: 5,888,806
[45] Date of Patent: Mar. 30, 1999

[54] TOWER REACTORS FOR BIOCONVERSION OF LIGNOCELLULOSIC MATERIAL

[76] Inventor: Quang A. Nguyen, 16458 W. 1st Ave., Golden, Colo. 80401

[21] Appl. No.: 878,037

[22] Filed: Jun. 18, 1997

Related U.S. Application Data

[62] Division of Ser. No. 780,943, Jan. 10, 1997.

[51] Int. Cl.[6] .............................. C12M 1/34; C12M 1/38
[52] U.S. Cl. ..................................... 435/291.3; 435/289.1; 435/290.1; 435/290.2; 435/291.1; 435/291.3; 435/291.5; 435/294.1
[58] Field of Search .............................. 435/289.1, 283.1, 435/165, 105, 290.1, 290.2, 291.3, 294.1, 291.1, 291.5

[56] References Cited

U.S. PATENT DOCUMENTS

| | | | |
|---|---|---|---|
| 4,654,308 | 3/1987 | Safi et al. | 435/294.1 |
| 5,141,861 | 8/1992 | Dale | 426/494 |
| 5,258,293 | 11/1993 | Lynd et al. | 435/165 |
| 5,348,871 | 9/1994 | Scott et al. | 435/165 |
| 5,424,417 | 6/1995 | Torget et al. | 536/56 |

OTHER PUBLICATIONS

Wieczorek et al. FEM Microbiol. Rev. vol. 14, pp. 69–74, 1994.
Reese et al. Enzyme Microbiol. Technol. vol. 2, pp. 239–240, 1980.
Mukataka et al. Ferment. Technol. vol. 61 (6), pp. 615–621, 1983.
Hinman et al. Appl. Bio. Biotech. vol. 34/35, pp. 639–649, 1992.

*Primary Examiner*—Leon B. Lankford, Jr.
*Assistant Examiner*—Christopher R. Tate
*Attorney, Agent, or Firm*—Ruth Eure; Biotechnology Patent Servives

[57] ABSTRACT

An apparatus for enzymatic hydrolysis and fermentation of pretreated lignocellulosic material, in the form of a tower bioreactor, having mixers to achieve intermittent mixing of the material. Precise mixing of the material is important for effective heat and mass transfer requirements without damaging or denaturing the enzymes or fermenting microorganisms. The pretreated material, generally in the form of a slurry, is pumped through the bioreactor, either upwards or downwards, and is mixed periodically as it passes through the mixing zones where the mixers are located. For a thin slurry, alternate mixing can be achieved by a pumping loop which also serves as a heat transfer device. Additional heat transfer takes place through the reactor heat transfer jackets.

7 Claims, 5 Drawing Sheets

TOWER REACTORS FOR BIOCONVERSION OF LIGNOCELLULOSIC MATERIAL

This application is a Divisional application of application Ser. No. 08/780,943 filed Jan. 10, 1997.

CONTRACTUAL ORIGIN OF THE INVENTION

This invention was made with Government support under Contract No. DE-AC36-83CH10093 awarded by the Department of Energy. The Government has certain rights in this invention.

FIELD OF THE INVENTION

This invention relates to the field of ethanol production from lignocellulosic material.

BACKGROUND OF THE INVENTION

Lignocellulosic materials, such as wood, herbaceous material, agricultural residues, corn fiber, waste paper, pulp and paper mill residues, etc. can be used to produce ethanol. Generally, production of ethanol from lignocellulosic material requires four major steps. These four steps are pretreatment, hydrolysis, fermentation and recovery.

The first of these steps, pretreatment is also known as pre-hydrolysis. During this step the lignocellulosic material is heated to break down the lignin and carbohydrate structure, solubilize most of the hemicellulose and make the cellulose fraction accessible to cellulase enzymes. This heating is done either directly with steam or in slurry. Also, a catalyst may be added to the material to speed up the reactions. Catalysts suitable for this include strong acids, such as sulfuric acid and $SO_2$, or alkalis, such as sodium hydroxide.

The second step is hydrolysis, more specifically enzymatic hydrolysis. After the pretreatment step, enzymes are added to the pretreated material to convert the cellulose fraction to glucose. This is also known as saccharification and is generally done in stirred-tank reactors or fermentors under controlled pH, temperature and mixing conditions.

The third step is fermentation of the sugars to ethanol. The sugars, released from the material as a result of the pretreatment and enzymatic hydrolysis, are fermented to ethanol by a fermenting organism, such as yeast, for example. The fermentation can also be carried out simultaneously with the enzymatic hydrolysis in the same vessels, again under controlled pH, temperature and mixing conditions. When saccharification and fermentation are performed simultaneously in the same vessel, the process is generally termed simultaneous saccharification and fermentation or SSF.

The fourth step is the recovery of the ethanol from the fermentation broth by distillation.

The enzymatic hydrolysis and fermentation processing steps have the following common requirements, particularly when the cellulosic material is in the form of a slurry:

The slurry is maintained at a set temperature for a predetermined time.

Adequate mixing is required to ensure effective and uniform heat and mass transfers. However, overly vigorous mixing can damage and denature the enzymes and fermenting organisms due to high shear. See Shear Inactivation of Cellulase of Trichoderma ressei by Reese and Ryu, *Enzyme Microb. Technol.*, July, 1980, Vol. 2, p. 239–240 and Effects of Agitation on Enzymatic hydrolysis of Cellulose in a Stirred-Tank Reactor by Mukataka, Tada and Takahashi, *Ferment, Technol.*, 1983, Vol. 61, no. 6, p. 615–621. Also, vigorous mixing requires large agitators and considerable power consumption which, in turn, significantly affects the economics of plant operation. Such economic considerations are quite considerable. For example, for a 2,000 ton/day plant, the capital cost of the SSF operation using continuous stirred-tank reactors (CSTR) in series was estimated at 16% of the fixed capital investment. See Preliminary Estimate of the Cost of Ethanol Production for SSF Technology by Hinman et al., *Appl. Bio. and Biotech.*, 1992, Vol. 34/35, p. 639–649. This value represents the third largest investment after pretreatment and utilities capital costs. The high capital cost of the fermentors is attributed to the large total SSF volume resulting from a typical 4–5 day retention time needed to complete the hydrolysis and fermentation using continuous stirred tank reactors connected in series. Based on pilot plant data and using a scale up exponent of 0.3, the mixing power requirement to keep pretreated sawdust particles (10 wt % insoluble solids) in suspension in a 1 million liter fermentor is estimated at 120 HP (or 0.5 HP/1000 gal). The estimated increase in mixing cost is $0.05/gal of ethanol when compared to the target mixing power of 0.1 HP/1000 gal. See Technical and Economic Analysis of an Enzymatic Hydrolysis Based Ethanol Plant—Draft by. Schell et al., 1991, SERI TP-232-4295, p. 54–55. This cost increase is significant for a process that is targeting $0.67/gal of ethanol as a cost goal. The projected high mixing energy requirement not only is costly but also presents a challenge in scaling up to very large-sized fermentors of 1 million gallons or larger, since the heat generated by the SSF process and by the agitators would be difficult to remove without using extensive cooling loops designed specifically for slurry. Depending on the extent of the cellulose hydrolysis and the lignin content in the material, the insoluble solid concentration in the SSF fermentors would gradually drop from about 12 wt % to only about 4 wt % in the last fermentor. As a result, there is a significant cost savings if the total volume of the fermentors and the mixing power requirement are reduced. These two factors form the basis for this invention.

DISCUSSION OF PRIOR ART

In conventional designs, the enzymatic hydrolysis and SSF fermentors are continuous stirred tank reactors (CSTR) arranged in series or cascade. Since this is a continuous process, the total volume of the CSTR can be very large because the enzyme hydrolysis process typically takes 4 to 5 days to complete in batch mode. Dependent on the number of reactors used, the residence time for a continuous cascade CSTR system is generally longer than in a batch mode to achieve the same degree of conversion because of back mixing of substrate. However, the volumetric productivity of the continuous cascade CSTR system is higher than that of a batch system because of the excessively long time required to fill and unload large batch fermentors. Other major drawbacks of CSTR include high mixing power requirements to maintain the undissolved solids in suspension and avoid dead space; vigorous mixing and long residence time would likely denature the enzymes requiring more enzyme be added to the system to effectively hydrolyze the cellulose. All of the above factors result in high capital and operating costs.

Plug-flow reactors have been recognized as having higher volumetric productivity than CSTR systems. For enzyme hydrolysis reactors, higher productivity translates into smaller reactor volume, shorter residence time and therefore less damage and denaturation of enzyme. It has been estimated that 20 fermentors in a cascade CSTR system would be required to approach the productivity of a plug flow reactor. See *Biochemical Engineering Fundamentals* by Bailey and Ollis, 1977, McGraw Hill, New York, p. 535–538. A variety of plug-flow reactors in the form of tower bioreactors have been proposed to improve ethanol productivity; however, these designs are suitable only for processing liquid substrates and not for slurries containing high concentrations of undissolved solids such as lignocellulosic materials.

Examples of these liquid-processing tower bioreactors include: U.S. Pat. No. 4,654,308 to Safi, Rouleau, and Mayer. This reference suggests a bioreactor with horizontal trays stacked in a vertical tower. The inventors suggest that the bioreactor may be used to ferment ethanol from wastewater from a pulp or paper plant, or to produce methane from cheese plant waste. The reactor of this reference is designed to handle aqueous solutions of sugars containing little undissolved solids. The slurries containing high insoluble solids for which the reactors of the present invention are designed will likely plug up the trays of this type of bioreactor.

Wieczorek and Michalski describe a tower fluidized-bed bioreactor in Continuous Ethanol Production by Flocculating Yeast in the Fluidized Bed Bioreactor *FEM Microbio Rev.*, 1994, vol. 14, p. 69–74. Continuous fermentation of molasses was carried out using a highly flocculent strain of yeast. This type of bioreactor is not suitable for processing biomass slurries since the solids, which are primarily in the form of undigested fibers and insoluble lignin, would likely wash the yeast or other fermenting organisms out of the bioreactor. Furthermore, like the stacked tray design described in U.S. Pat. No. 4,654,308, this type of bioreactor does not provide adequate mixing necessary for enzymatic hydrolysis.

SUMMARY OF THE PRESENT INVENTION

It is an object of the present invention to provide an improved economical method and apparatus for the conversion of lignocellulosic material to ethanol.

It is a further object of the present invention to provide a method and apparatus for the conversion of lignocellulosic material comprising reduced total fermentor volume.

It is a further object of the present invention to provide a method and apparatus for the conversion of lignocellulosic material comprising reduced mixing power consumption.

The apparatus of the present invention comprises a tower bioreactor (hereinafter also referred to as tower or bioreactor) which is suitable for continuous enzymatic hydrolysis or SSF of pretreated lignocellulosic material in a near plug flow mode. The movement of liquid relative to undissolved solids is mainly concurrent. Side-entry mixers are strategically located on the side of the tower bioreactors to ensure uniform heat and mass transfer, to prevent channeling where liquid bypasses solids, and to minimize shear that may denature and damage the enzymes and fermenting microorganisms. A small amount of back mixing takes place at or near the mixers, but most of the slurry moves forward in a near plug flow mode. The side-entry mixers are used to generate an intermittent mixing regime inside the tower bioreactors. Although the mixers operate continuously, intermittent mixing is achieved when the slurry passes through alternating mixing zones and non-mixing zones inside the towers. Intermittent mixing achieves essentially the same rate of hydrolysis as continuous mixing, but at reduced overall mixing power consumption. Temperature control of the reaction is achieved by circulating heating or cooling fluid through the heat transfer jacket. For a lower viscosity slurry where the slurry can be readily pumped through heat exchangers, temperature control and mixing can be achieved by way of external heat exchange loops.

The novel features of this invention include the strategic location of the mixers or mixing loops and heat transfer zones for obtaining optimal mass and heat transfer and avoiding channeling effects with reduced mixing power consumption. The near plug flow design minimizes back mixing, thus increasing product concentration and conversion efficiency as compared to a completely-mixed bioreactor commonly used in a cascade CSTR system. The intermittent mixing also imparts less overall shear to the enzymes in comparison with continuous mixing; and as a result, denaturation and damage to enzymes is reduced.

DETAILED DESCRIPTION OF EMBODIMENTS OF THE INVENTION

Figure 1:
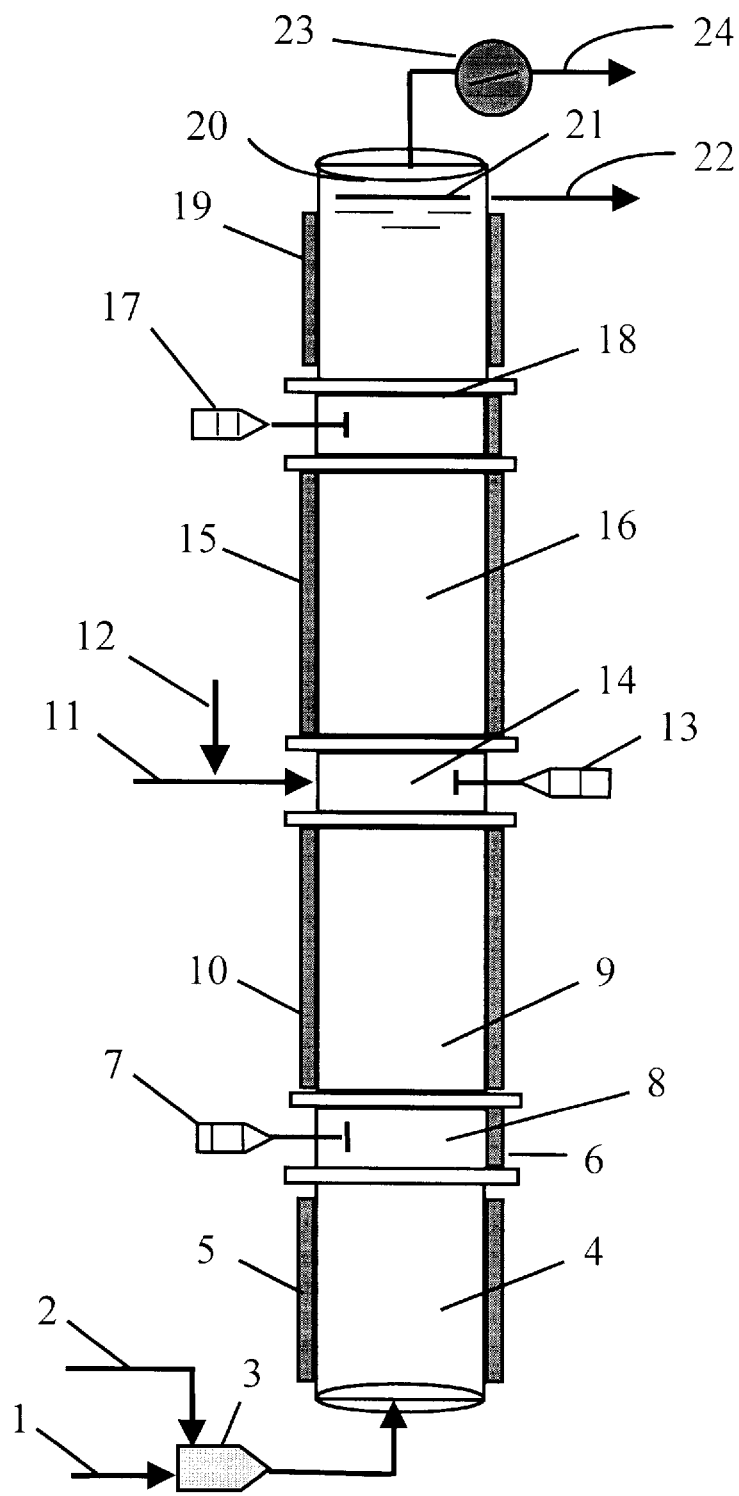
FIG. 1 shows a schematic diagram of a typical tower bioreactor equipped with side-entry mixers for enzyme hydrolysis or fermentation of pretreated lignocellulosic material at high solid loading, which is defined herein as a feed stream containing greater than about 10 wt % total suspended solids.
Figure 2:
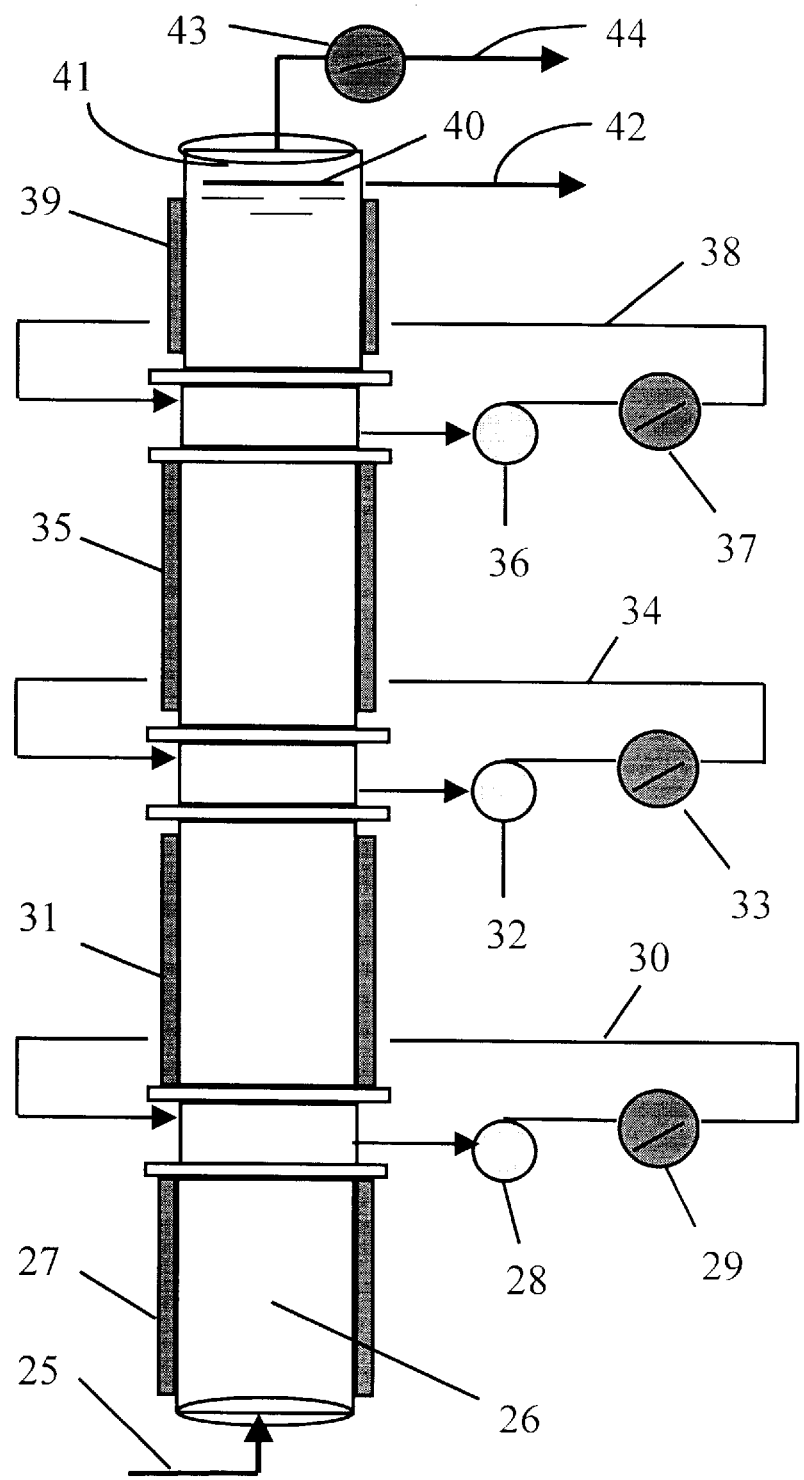
FIG. 2 shows a schematic diagram of a typical tower bioreactor equipped with mixing and heat transfer loops for enzyme hydrolysis or fermentation of pretreated lignocellulosic material at medium solid loading which is defined herein as a feed stream containing about 5–10 wt % total suspended solids.
Figure 3:
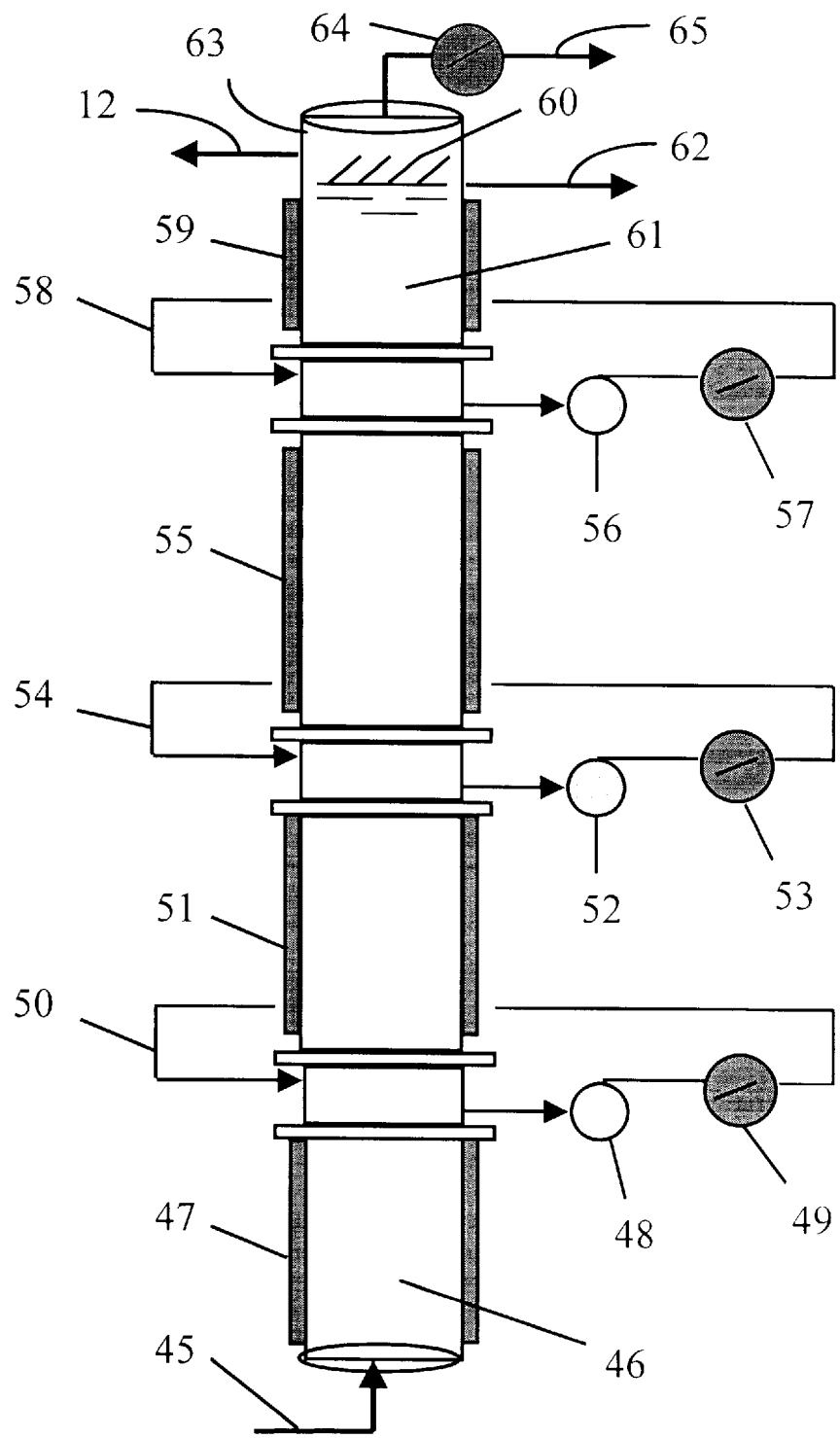
FIG. 3 shows a schematic diagram of a typical tower bioreactor equipped with mixing and heat transfer loops for enzyme hydrolysis or fermentation of pretreated lignocellulosic material at low solid loading which is defined herein as a feed stream containing less than about 5 wt % total suspended solids.

In the enzymatic hydrolysis (or SSF) of pretreated lignocellulosic material, the viscosity of the slurry inside the bioreactors decreases with time as the cellulose fibers are hydrolyzed into soluble glucose. However, the viscosity of the slurry is still high since all fibers are not digested and the insoluble lignin is not digestible by the enzymes, as compared to fermentation of sugar solutions such as molasses. Therefore, to factor in this reduction in viscosity of the fermentation broth, the tower bioreactor design is arbitrarily divided into three categories: high-solids having greater than about 10 wt % undissolved solid concentration, medium-solids having between about 5 wt % and 10 wt % undissolved solid concentration and low-solids, having less than about 5 wt % undissolved solid concentration. Exemplary designs for these configurations are shown in FIGS. 1, 2, and 3, respectively. In high-solids bioreactors, mixing is achieved mostly by agitators, whereas, in medium-solids or low-solids bioreactors, mixing can also be achieved by pumping loops, also referred to herein as mixing loops. The mixing of the slurry also serves to pump the slurry. As used herein, mixing until blended means that the solid particles move relative to each other in random direction; therefore a blended slurry as a whole has a uniform consistency. The advantage of using pumping loops is that heat exchangers can be installed in the loops for enhanced temperature control of the fermentation. Since each of these three designs has its own parameters, they will be discussed separately. High-solids tower bioreactors FIG. 1 shows a typical high-solids tower bioreactor which is suitable for use at the beginning of the enzymatic hydrolysis or SSF process where approximately less than 50% of the cellulose is hydrolyzed to glucose upon leaving the bioreactor. For example, this high-solids bioreactor can be used in the first stage in a four-stage tower bioreactor system in series with a total residence time of four days (see FIG. 4).

FIG. 1 shows the slurry feed coming into the bottom of the bioreactor for upward directional flow. It should be noted, however the inlet can also be at the top of the bioreactor, in which case the slurry flow is in the downward direction, but for purposes of this description an upward flow will be described. The description of the operation of the tower bioreactor using a downward directional flow will be obvious to the skilled artisan by reversing the sequence of the upward directional flow description. Depending on the hydraulic retention time and the height of the tower, the bioreactor may have more mixing zones, as shown. Typically, the volume of each bioreactor can be as large as 2 million liters. The hydraulic retention time in each bioreactor can be up to 24 hours. The height-to-diameter ratio can vary between about 3 and 10 but is preferably kept between about 4 and 5 to limit the height of large bioreactors. Too low a height-to-diameter ratio may cause ineffective mixing or back mixing. For example, for a 2 million liter bioreactor, the height could be about 40 meters and the inside diameter could be approximately 8 meters. For a 1 million liter bioreactor, the height could be about 30 meters and the diameter could be about 6.6 meters.

The slurry of pretreated lignocellulosic material is pumped through line 1 into mixer 3 where enzymes and nutrients are also added through line 2 and blended with the slurry. The solids loading of the slurry entering the mixer vary between about 10 to 25 wt %, more preferably between about 15–20 wt %. The mixer ensures enzyme and nutrients are uniformly distributed throughout the slurry. The residence time in the mixer is typically less than about 10 minutes. The mixer also serves as a pump that pushes the slurry into the bottom of tower bioreactor 4 and conveys the slurry through the tower. The tower bioreactor is equipped with heat transfer jackets 5, 6, 10, 15 and 19, through which heat transfer fluid can be circulated to control the temperature inside the tower bioreactor. The heat transfer jackets are divided into zones such that the temperature in each zone can be controlled independently. This feature provides an option to create a temperature gradient along the height of the bioreactor. In general, most fungal cellulase enzymes hydrolyze cellulose most effectively between about 45° and 50° C.; however most ethanol fermenting organisms such as yeast are most effective between about 30°–34° C. As a compromise most SSF processes use temperatures in the 35°–38° C. range. The temperature gradient capabilities of the present invention allow for optimization of enzymatic hydrolysis and fermentation by allowing each of these processes to take place at or near their optimal temperatures. In the first stage of a four-stage SSF bioreactor system, the inlet of the bioreactor is operated at about 40°–50° C., or within the optimal temperature range for the cellulase enzymes used, to maximize the hydrolysis rate. The fermenting organism is not introduced at this high-temperature zone of the bioreactor. The enzyme hydrolysis process reduces the viscosity of the slurry, thus improving its mixing, pumping and heat transfer properties. As the slurry travels up the tower bioreactor, it passes through hydrolysis sections and SSF sections, within each of these sections are mixing zones. All of these zones and sections are temperature controlled by heat transfer jackets. Experimental results indicate that for enzymatic hydrolysis of a 10 wt % slurry of cellulose in shake flasks, intermittent mixing for 5 minutes at 2 hour intervals for the first 12 hours, followed by mixing intervals of 5 minutes every 8–12 hours gave essentially the same hydrolysis rate and glucose yield as continuous mixing (See FIG. 5). These results suggest that since enzyme hydrolysis rate is relatively slow, continuous mixing to improve mass and heat transfer is not necessary. Frequent mixing is required at the beginning phase of hydrolysis when the viscosity of the slurry is high. In this example, the initial mixing takes place at two hour intervals. Afterwards, the mixing frequency can be reduced to one mixing cycle per 4–12 hours without significant reduction in the hydrolysis rate.

Figure 4:
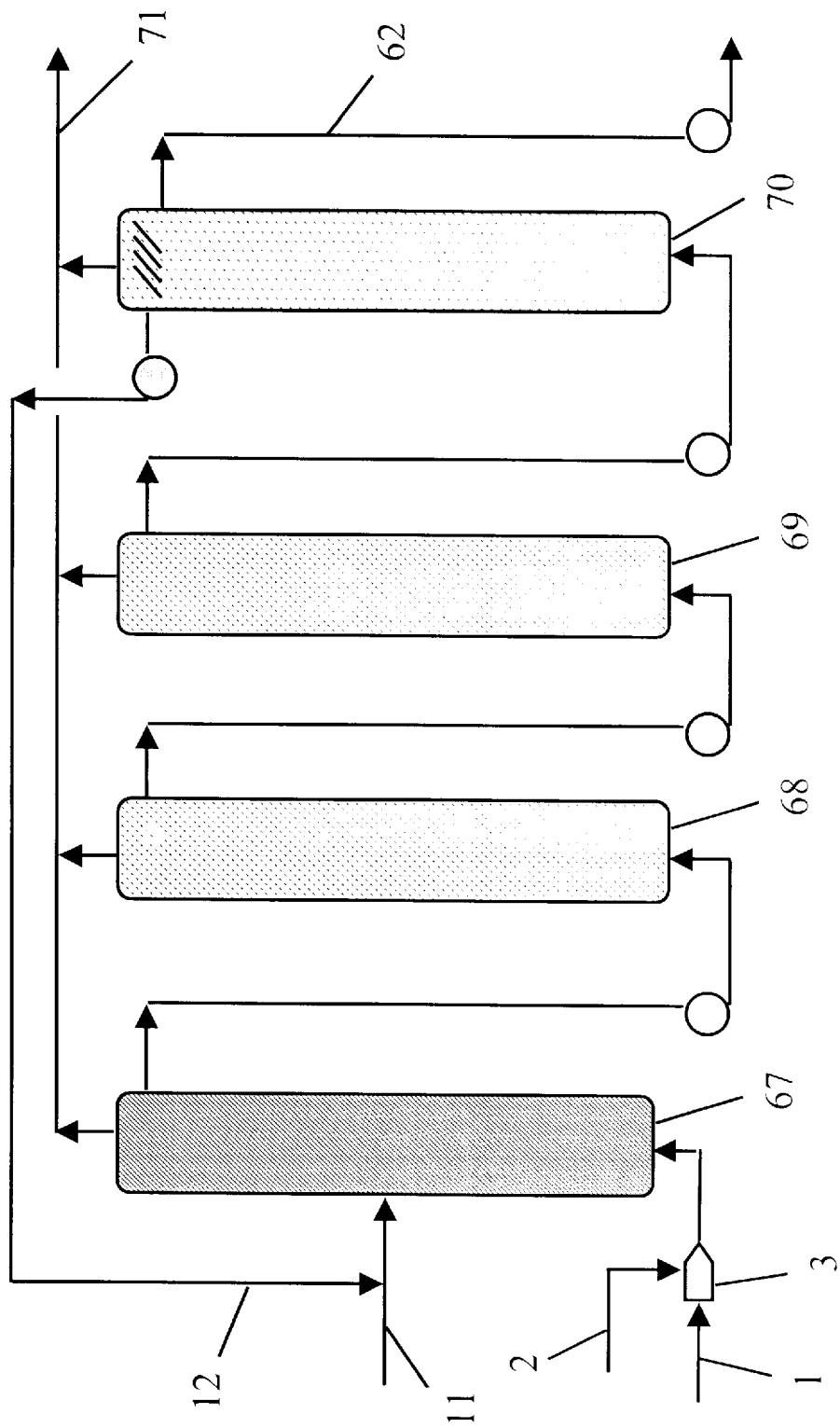
FIG. 4 shows a schematic diagram of a typical four-stage bioreactor system for enzymatic hydrolysis or SSF of pretreated lignocellulosic material. The system consists of high-, medium-, and low-solid tower bioreactors connected in series. Depending on the throughput and size of the bioreactors, each stage can have one, two or more bioreactors connected in parallel.

The effect of intermittent mixing is achieved in the tower bioreactor mixing zones 8, 14 and 18 by agitators 7, 13, and 17 in FIG. 1. To achieve the same effect as continuous mixing, the mixing intervals must be adjusted according to the viscosity of the slurry, the degree of mixing (or mixing powers), the types of mixers used and the heat transfer required. Since the position of the mixers or mixing loops on tower bioreactors can not be readily changed during operation, the size of the mixing zone and the mixing intensity in the zones can be varied by changing the speed of the mixer or the impeller design. Lower intensity mixing occurs between mixing zones due to movement of the slurry conveyed by the mixer 3. There are also transition areas immediately above and below each mixing zone where intermediate intensity mixing occurs. In high-solids tower bioreactors, particularly in the first 12 hours of hydrolysis, the agitators or mixers are located fairly close together to achieve about 2 to 4 hours retention time between mixing zones. Depending on the size of the tower bioreactor, design and power of the agitator, each mixing zone may contain one or more agitators. The objective is to achieve complete suspension and motion of the solid particles relative to each other or blending of the slurry in the mixing zone. Blended slurry has uniform consistency throughout. The agitator blades can be of various configurations such as marine impellers, turbines, helical or anchor impellers, for example. Helical and anchor impellers are preferred to because, generally, they require less power and generate less shear than other designs. After about 6 to 8 hours in first and second hydrolysis sections 4 and 9, respectively, where the heat transfer jacket 5 maintains the temperature of the slurry at about 45° C., the partly digested slurry enters mixing zone 14 where yeast or other fermenting organism is added through line 11. There may be more than one mixing zone in each hydrolysis section, as shown in FIG. 1. Using temperature control zones in heat transfer jacket 10, the temperature of the slurry is gradually lowered from about 45° C. at the inlet of the tower bioreactor to about 37° C. (or near the optimal temperature for the SSF process) in mixing zone 14. Recycled enzyme and fermentation organisms from the last stage of the SSF system are also introduced into this mixing zone through line 12. Above second hydrolysis section 9 is the SSF section 16, where hydrolysis and fermentation take place simultaneously. There may be more than one mixing zone in the SSF section, as shown in FIG. 1. The interval between mixing zones in the SSF sections vary between 3 hours and 5 hours depending on the viscosity of the slurry. The higher the viscosity, the shorter the intervals between mixing zones. The viscosity decreases as the slurry passes through the sequential stages of the system. This is depicted in FIG. 4, which shows a 4-stage system.

The partly hydrolyzed slurry is withdrawn at the top of the tower bioreactor through line 22 and pumped to the next bioreactor in series (i.e., in stage 2). An auger can be installed at the tower outlet to facilitate the withdrawal of the slurry through line 22. A level controller is used to established a level 21 in the tower. Carbon dioxide generated during fermentation, entrained air and other gases are collected in the tower overhead space 20. The gases are vented out of the tower by way of ethanol condenser 23 and line 24.

Medium-solids tower bioreactors

FIG. 2 shows a typical tower bioreactor for a slurry having medium suspended solid concentration. These bioreactors are suitable for use in series after the high-solids bioreactors, i.e., in the intermediate stages of the enzymatic hydrolysis or SSF process. As depicted in FIG. 4, the intermediate stages, namely the second stage or tower 68 and third stage or tower 69, consist of one or more pairs of bioreactors connected in series. Returning to FIG. 2, partly digested slurry is pumped from the exit of the high-solids bioreactor into the inlet of the medium-solids bioreactor 26 through line 25. For a downflow tower bioreactor, the inlet would be at the top. However, for consistency of description, an upward flow is described. As the slurry moves up the tower bioreactor, temperature control is achieved by way of heat transfer jackets 27, 31, 35 and 39. Depending on the viscosity of the slurry, mixing can be done by mixing loops 30, 34 and 38 instead of agitators. Medium-solids bioreactors may be equipped with both agitators and mixing loops. In the mixing loops, part of the slurry is pumped out of the tower bioreactor by pumps 28, 32 and 36 through optional heat exchangers 29, 33 and 37, respectively and then returned to the tower bioreactor above the pump suction points. The mixing loops 30, 34 and 38 with external heat exchangers can effect better temperature control than using the heat transfer jackets alone.

The mixing loops are positioned to achieve a retention time of about 3 to 6 hours between mixing zones. As the viscosity of the slurry decreases with time (i.e., in the third stage bioreactors) the interval between mixing loops may be increased to 4 to 7 hours.

The partly hydrolyzed slurry is withdrawn at the top of the tower bioreactor through line 42 and pumped to the next bioreactor in series, either in the third stage or fourth stage. A level controller is used to establish a level 40 in the tower bioreactor. Carbon dioxide generated during fermentation and entrained air and other gases are collected in the tower bioreactor overhead space 41. The gases are vented out of the bioreactor by way of ethanol condenser 43 and line 44.

Low-solids tower bioreactors

FIG. 3 shows a schematic diagram of a bioreactor for slurry having low solids concentration. A notable difference between this tower bioreactor and its higher solids counterparts is this bioreactor is equipped with a solid settler to facilitate the separation of cells of yeast or other fermenting microorganism from residual insoluble solids. This low-solids tower bioreactor is suitable for use in series after the medium-solids bioreactors, i.e., in the final stage of the enzymatic hydrolysis or SSF process. The low-solids bioreactors have similar design and operation as the medium-solids bioreactors, i.e., mixing loops are used, but the interval between mixing loops is increased to 6 to 10 hours.

Slurry exiting from a medium-solids tower bioreactor is pumped into the low-solids reactor 46 through line 45. The low-solids tower bioreactors are equipped with heat transfer jackets 47, 51, 55 and 59, mixing loops 50, 54 and 58, mixing pumps 48, 52, and 56, and external heat exchangers 49, 53 and 57. In addition, these low-solids bioreactors are equipped with a solid settler 60 at the top of the settling zone 61 to separate the enzymes and cells of fermenting organisms from residual insoluble solids for recycling back to the high solids or first stage bioreactors. An example of solid settler 60 is inclined plates. The slurry is retained in settling zone 61 for up to about 6 hours to ensure sufficient time for the residual solids to separate from the microbial cells. The fermentation broth is withdrawn from the bioreactor by line 62 at the bottom of the solid settler. The broth is forwarded to the ethanol recovery system (not shown). The recycled cells and enzyme stream is withdrawn at the top of the solid settler through line 12 and returned to the first stage bioreactors. The volume of the recycle stream is typically 10–15% of that of the fermentation broth stream. Evolved carbon dioxide is collected in the overhead space 63 and vented out of the bioreactor by way of condenser 64 and line 65.

SSF tower bioreactor system

FIG. 4 shows a typical four-stage SSF system utilizing upflow tower bioreactors. Pretreated biomass slurry 1 and enzymes 2 are blended together in mixer 3 before entering the first-stage high-solid tower bioreactor 67. The bottom third to half of the first-stage tower bioreactors are hydrolysis sections. Fermentation organisms are initially added at the entry of the SSF section through line 11. Recycled enzyme and fermentation organisms are also added through line 12. Second- and third-stage towers 68 and 69, respectively, are normally medium-solids bioreactors utilizing mixing loops or a combination of agitators and mixing loops. The final stage tower 70 normally operates at low solids concentration to facilitate separation of microbial cells from residual solids at the top of the towers. Fermentation broth is withdrawn from the system through line 62 and sent to the ethanol recovery system (not shown). Carbon dioxide and entrained air and other gases are vented from the system through line 71.

Figure 5:
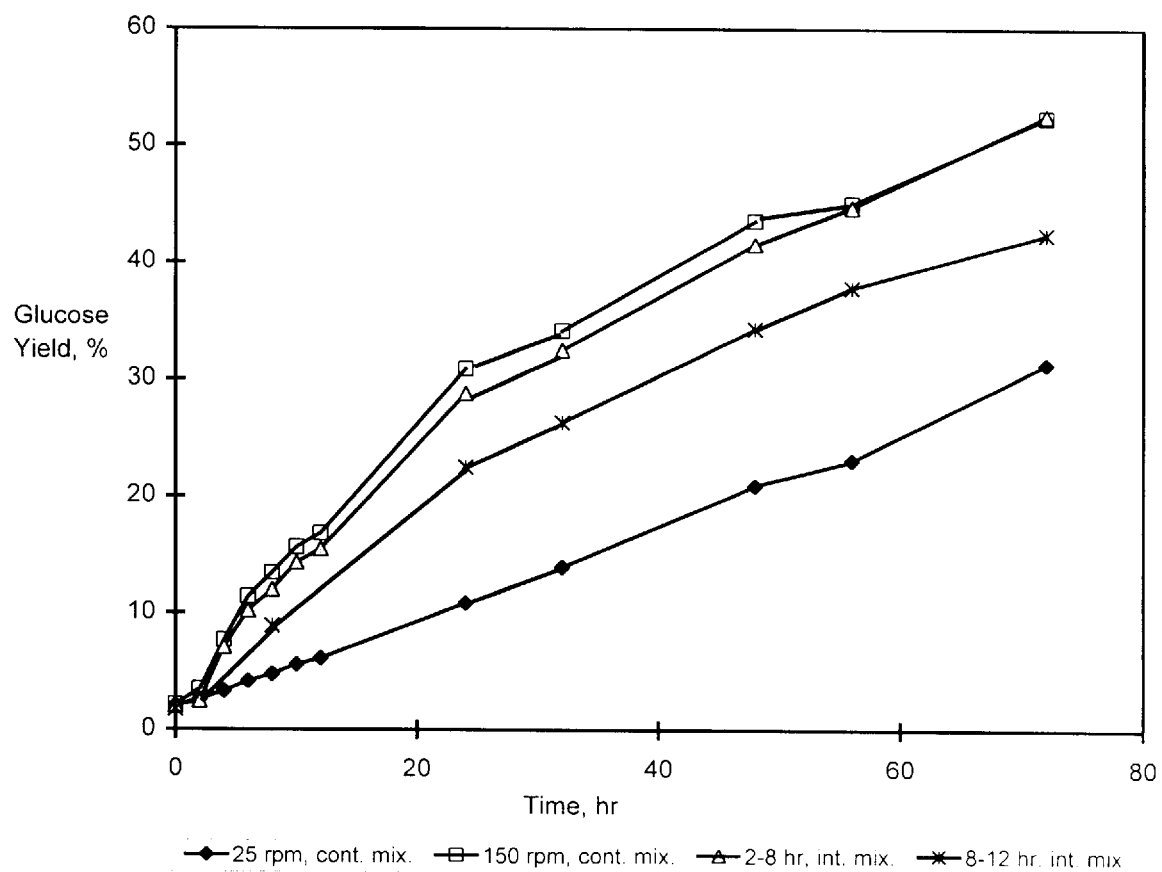
FIG. 5 is a graph illustrating the effect of mixing on enzymatic hydrolysis of alpha cellulose.

FIG. 5 is a graphical representation showing results of experiments conducted to demonstrate intermittent mixing compared with continuous mixing. In these experiments, 250 mL of 10 wt % cellulose slurry was placed in 500 mL Erlenmeyer flasks at the beginning of the hydrolysis. Cellulase enzymes were added to the flasks using a loading of 25 filter paper unit per gram of cellulose (FPU/g cellulose). The flasks were prepared in duplicate, and were placed in orbital shakers set at 45° C. and predetermined speeds. Small samples were withdrawn from the flasks as needed for determination of glucose released by the enzymatic hydrolysis. Before a sample was withdrawn, the contents of the flask were mixed thoroughly to ensure uniformity. In continuous mixing mode, mixing at 150 revolutions per minute (rpm) gave significantly higher glucose yield and hydrolysis rate than mixing at 25 rpm. At 150 rpm, the slurry appeared to be thoroughly mixed, i.e., the cellulose particles were fully suspended and in motion. At 25 rpm, the cellulose particles settled to the bottom of the flask, and a distinct layer of liquid was observed above the solids. Intermittent mixing for 5 minutes at 150 rpm then reduced to 25 rpm for 2 hours for the first 12 hours then 5 minutes at 150 rpm every 8 to 12 hours thereafter for an additional 60 hours gave essentially the same hydrolysis rate as continuous mixing at 150 rpm for 72 hours. When the mixing interval was increased to 8 to 12 hours throughout the hydrolysis (i.e., mix at 150 rpm for 5 minutes every 8–12 hours), the hydrolysis rate was moderately reduced. Each data point on the intermittent mixing lines shown in FIG. 5 represents a 5 minute mixing period at 150 rpm, and for the periods between these data points the slurries were mixed at 25 rpm. These experimental results indicate that frequent and high initial mixing rpm at the beginning of the hydrolysis when viscosity of the slurry is high is required to obtain as high a hydrolysis rate as is obtainable by continuous mixing. Once the viscosity of the slurry is reduced, the frequency of vigorous mixing can be reduced to 8 to 12 hours.

All publications and patents mentioned in the above specification are herein incorporated by reference. Various modifications and variations of the described invention will be apparent to those skilled in the art without departing from the scope and spirit of the invention. Although this invention has been described in connection with specific preferred embodiments, it is to be understood that the invention as claimed should not be unduly limited to such specific embodiments. Indeed, various modifications of the described modes for carrying out the invention which are obvious to those skilled in the art of fermentation of biomass to ethanol or related fields are intended to be within the scope of the following claims.

I claim:

1. A tower bioreactor for converting pretreated lignocellulosic material to ethanol comprising at least two or more sequential mixers, at least two or more mixing zones, at least one hydrolysis section and at least one simultaneous saccharification and fermentation (SSF) section wherein the location of said two or more sequential mixers causes uniform heat and mass transfer, prevents channeling, and achieves intermittent mixing of the material wherein the distance between the two or more mixing zones is determined by the formula D=tx Q/A wherein D is the distance between mixing zones, Q is the average volumetric flow rate of slurry being pumped through the bioreactor, t is the time interval between mixing zones and A is the cross-sectional area of the bioreactor.

2. The tower bioreactor of claim 5 wherein the mixers are mixing loops.

3. The tower bioreactor of claim 5 also comprising a solid settler.

4. The tower bioreactor of claim 5 having a height-to-diameter ratio of about 5 to 1.

5. The bioreactor of claim 1 for use with lignocellulosic material having concentration of undissolved solids in the slurry greater than 10%, wherein t is about 2 to about 3 hours.

6. The bioreactor of claim 1 for use with lignocellulosic material having concentration of undissolved solids in the slurry less than 10%, wherein t is about 3 to about 8 hours.

7. The bioreactor of claim 1, wherein at least one of the two or more mixers is selected from the group consisting of side entry mixers, top entry mixers and bottom entry mixers.

* * * * *